United States Patent [19]
Brooks

[11] Patent Number: 5,280,790
[45] Date of Patent: Jan. 25, 1994

[54] AUTOMATIC BLOOD PRESSURE MONITOR HAVING REDUCED DATA LOSS SENSITIVITY TO CUFF PRESSURE CHANGES

[75] Inventor: James R. Brooks, Washington, Oreg.

[73] Assignee: SpaceLabs Medical, Inc., Redmond, Wash.

[21] Appl. No.: 8,731

[22] Filed: Jan. 25, 1993

[51] Int. Cl.$^5$ ............................................. A61B 5/00
[52] U.S. Cl. .................................. 128/681; 128/682; 364/413.03
[58] Field of Search ..................... 128/672, 677–686; 364/413.05

[56] References Cited

U.S. PATENT DOCUMENTS 5,054,494 10/1991 Lazzaro et al. ..................... 128/681

Primary Examiner—Lee S. Cohen
Assistant Examiner—Robert L. Nasser, Jr.
Attorney, Agent, or Firm—Seed and Berry

[57] ABSTRACT

An automatic blood pressure monitor having a blood pressure cuff, an air pump applying pressurized air to the cuff, an air valve selectively venting the cuff, and a pressure transducer generating an output signal having a D.C. component indicative of the steady-state pressure in the cuff, and an A.C. component indicative of oscillometric pulses. The pressure transducer output is amplified and applied to an analog-to-digital converter which generates a digital word indicative of the steady-state cuff pressure. The amplified pressure transducer output is also applied to one input of a differential amplifier having an output that is applied to an analog-to-digital converter having a limited operating range. The other input of the amplifier receives an offset signal from a voltage source to offset the amplified pressure transducer output so that the output of the differential amplifier will not exceed the operating range of the analog-to-digital converter.

9 Claims, 5 Drawing Sheets

AUTOMATIC BLOOD PRESSURE MONITOR HAVING REDUCED DATA LOSS SENSITIVITY TO CUFF PRESSURE CHANGES

TECHNICAL FIELD

This invention relates to automatic blood pressure monitors, and more particularly, to an automatic blood pressure monitor that minimizes the loss of oscillometric data caused by changes in the cuff pressure.

BACKGROUND OF THE INVENTION

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the brachial artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to a blood pressure cuff extending over the artery as minute changes in the cuff pressure, which are known as oscillometric pulses. Automatic blood pressure monitors employing the oscillometric method measure and record the amplitude of the oscillometric pulses at a number of cuff pressures. After the blood pressure measurement had been completed, a table contains the oscillometric pulse amplitudes recorded at each cuff pressure.

In theory, the systolic, diastolic, and mean arterial blood pressures can then be determined from the values in the table using theoretical and/or empirical definitions of these parameters as a function of the amplitudes of these oscillometric pulses. However, blood pressure measurements are often adversely affected by artifact, generally produced by patient movement. Motion-induced artifact can substantially alter the measured amplitude of oscillometric pulses, thus introducing inaccuracies in the measurement of the patient's blood pressure.

Another problem associated with automatic blood pressure monitors using the oscillometric method occurs when the cuff pressure is changed from one pressure to another, particularly if the pressure is incrementally changed at a relatively high rate. The cuff pressure consists of two components, a relatively constant, or "DC", component and a relatively variable, or "AC", component. The relatively constant component defines the occlusive force of the blood pressure cuff, while the relatively variable component is produced by the oscillometric pressure pulses following each contraction of the heart.

The cuff pressure and the oscillometric pulses are typically sensed by a pressure transducer of conventional variety. The pressure transducer outputs a signal having two components which, like the pressure in the cuff itself, consist of a D.C. or relatively constant component indicative of the occlusive force, and an A.C. or relatively variable component corresponding to the oscillometric pulses imparted to the cuff. The relatively constant D.C. component can be used as an indication of occlusive force on the artery beneath the cuff, while the relatively variable A.C. component represents the oscillometric signal.

The magnitude of the relatively constant pressure is very much greater than the magnitude of the pressure changes corresponding to the oscillometric pulses. As a result, the amplitude of the D.C. component in the transducer output signal, as well as the change in the D.C. component when the cuff pressure is changed, is very much greater than the amplitude of the A.C. component in the transducer output signal. When the cuff pressure is changed, a transient A.C. component is generated that is so much larger than the normal A.C. component resulting from the oscillometric pulses that the circuits which respond to the oscillometric pulses are overloaded or are otherwise unable to process oscillometric pulses following a change in cuff pressure. A similar phenomena can occur as a result of motion artifact or from pneumatic leaks in the cuff or components in fluid communication with the cuff. As a result, oscillometric data are lost for a period of time following a cuff pressure change, thus prolonging the time needed to obtain a blood pressure measurement.

SUMMARY OF THE INVENTION

The primary object of the invention it to provide an automatic blood pressure monitor that is able to obtain oscillometric pulse data immediately following a relatively large change in cuff pressure.

This and other objects of the invention are provided by a blood pressure monitor having such conventional components as a blood pressure cuff, an air pump applying pressurized air into the cuff, an air valve selectively venting the cuff to atmosphere, and a pressure transducer generating a pressure signal indicative of both the steady state fluid pressure in the cuff corresponding to an occlusive pressure exerted by the cuff, and a transient fluid pressure in the cuff indicative of the amplitude of an oscillometric waveform. The pressure transducer generates an output signal having a D.C. component corresponding to the steady state fluid pressure in the cuff, and an A.C. component indicative of the amplitude of an oscillometric waveform. The monitor includes a voltage source generating an offset voltage corresponding to the D.C. component of the pressure signal output by the pressure transducer. An offset generator amplifies the output of the pressure transducer and produces an offset pressure signal corresponding to the difference between the offset voltage and the amplified pressure signal. The offset pressure signal produced by the offset generator is sampled by an analog-to-digital converter having a predetermined operating range, thereby generating a plurality of digital words corresponding to a respective plurality of samples of the amplified offset pressure signal. These digital words are read by a processor which analyzes the samples to determine the blood pressure in an artery beneath the cuff. As a result, oscillometric pressure pulses imparted to the cuff can be sampled despite relatively large changes in the steady state fluid pressure in the cuff.

The processor preferably adjusts the magnitude of the offset signal by first comparing each sample of the amplified offset pressure signal to the operating range of the analog-to-digital converter. The processor then adjusts the offset signal in the event that a sample of the amplified offset pressure signal is outside a predetermined portion of the operating range of the analog-to-digital converter so that the amplified offset pressure signal is closer to the center of the operating range of the analog-to-digital converter.

The processing means preferably generates samples of an oscillometric waveform by summing the output of the analog-to-digital converter with a digital offset value to obtain each sample. The digital offset value is adjusted each time the value of the offset voltage is adjusted by summing the previous digital offset value with the difference in the output of the analog-to-digital converter before and after the offset voltage adjustment.

DETAILED DESCRIPTION OF THE INVENTION

Figure 1:
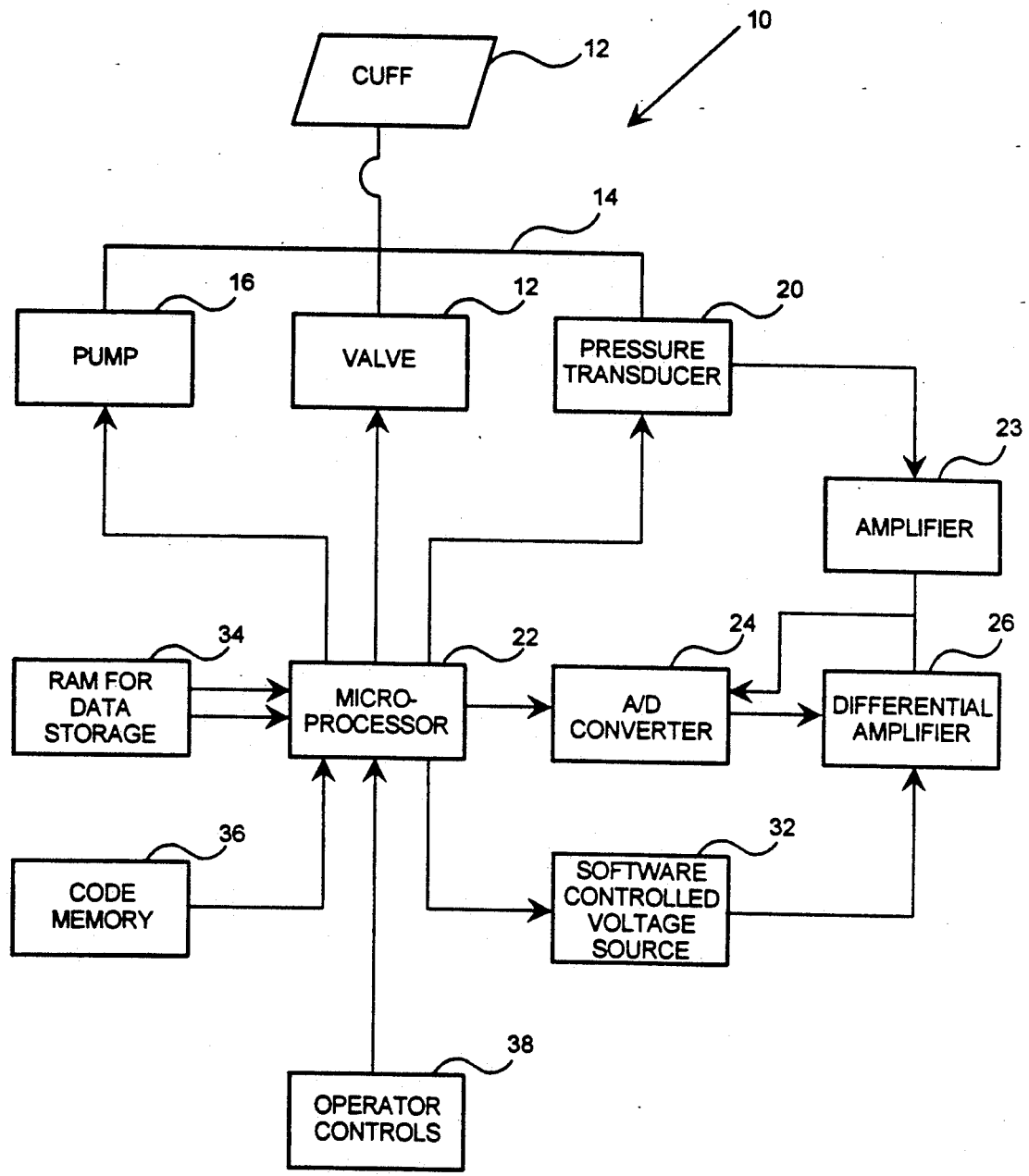
FIG. 1 is a block diagram of a presently preferred embodiment of an automatic blood pressure monitor having means for minimizing the loss of data during changes in cuff pressure.

One embodiment of an automatic blood pressure monitor 10 using the inventive technique to minimizes the loss of oscillometric data during changes in cuff pressure is illustrated in FIG. 1. The monitor 10 is composed of a number of hardware components, all of which are conventional. The monitor 10 includes a conventional blood pressure cuff 12 in fluid communication through tubes 14 with a conventional pump 16, a conventional solenoid valve 18, and a conventional pressure transducer 20. The pump 16 and solenoid valve 18 are electrically connected to respective output ports of a conventional microprocessor 22 which controls the operation of the pump 16 and solenoid valve 18 in a conventional manner.

During the operation of the automatic blood pressure measuring system, the pump 16 inflates the blood pressure cuff 12 to a pressure that is greater than the expected systolic pressure, as indicated by the pressure transducer 20. The solenoid valve 18 is then opened, usually for a predetermined period, although it may be continuously open to allow a slight leakage of air from the blood pressure cuff 12. However, the solenoid valve 18 normally allows air to escape from the cuff 12 fairly rapidly in relatively small increments. As the pressure in the cuff 12 is reduced, either gradually or incrementally, the pressure in the cuff 12 is measured by the pressure transducer 20.

As mentioned above, the pressure in the blood pressure cuff 12 consists of two components, namely, a relatively constant, or "DC", component and a relatively variable, or "AC", component. The relatively constant component defines the occlusive force of the blood pressure cuff 12. The relatively variable component is produced by the minute change in the pressure of the cuff 12 following each contraction of the heart. Thus, the relatively constant DC component of the pressure in the cuff can be used as an indication of cuff pressure, while the relatively variable AC component of the pressure in the cuff 12 represents the oscillometric signal.

A signal from the pressure transducer 20 is applied to a conventional analog-to-digital ["A/D"] converter 24 through a first amplifier 23 and a differential amplifier 26. In the presently preferred embodiment of the invention, the amplifier 23 generates a signal that varies between 0–5 volts as the pressure in the cuff 12 varies between 0–300 mm. of mercury. Thus, the signal at the output of the amplifier 23 has a slope of 60 mm./volt. The output of the amplifier 23 is used as a "cuff pressure signal" to provide an indication of the steady state pressure in the cuff 12. In the presently preferred embodiment of the invention, the differential amplifier 26 boosts the output of the pressure transducer 20 so that its output varies between 0–5 volts as the pressure in the cuff 12 varies over a range of 7 mm. of mercury. Thus, the signal at the output of the differential amplifier 26 has a slope of 1.4 mm./volt. The output of the differential amplifier 26 is used as the "oscillometric signal" from which that patient's blood pressure is determined.

The A/D converter 24 has two input channels for alternately digitizing either the output of the pressure transducer 20 or the output of the differential amplifier 26, and alternately applying respective digital words to the microprocessor 22. The A/D converter 24 used in the presently preferred embodiment of the invention outputs a 10 bit digital word which can divide the analog input into 1024 values. The resolution of the signal at the output of the A/D converter 24 is thus about 293 $\mu$m. (i.e. 300 mm./1024) for the cuff pressure signal and 6.8 $\mu$m (i.e. 7 mm./1024) for the oscillometric signal.

In many modern blood pressure devices, the A/D converter 24 is actually contained on the microprocessor chip. Whether the A/D converter 24 is on the microprocessor chip or whether it is located on a separate chip, the microprocessor 22 has access to a digitized signals indicative of the cuff pressure and the oscillometric signal. The microprocessor 22 thus extracts the two components of the pressure in the blood pressure cuff namely (a) the pressure within the cuff and (b) the minute change in the pressure of the cuff following each contraction of the heart. Alternatively, separation of the cuff pressure into these two components can be accomplished by external hardware filters, as is quite common in older automatic blood pressure monitors. Whether the separation is accomplished by external hardware filters or by an algorithm internal to the microprocessor 22 is not important for the current invention.

During a blood pressure measurement, the pressure in the cuff 12 (FIG. 1) is typically changed in pressure increments that are well in excess of 10 mm. of mercury. It will be apparent that a change in 10 mm should cause the output of the differential amplifier to change by over 7 volts (i.e., [5 volts/7 mm.]* 10 mm.). Yet the maximum output of the differential amplifier 26 is 5 volts. It is thus apparent that the differential amplifier 26 and A/D converter 24 would be incapable of processing oscillometic pulses after the pressure in the cuff was changed by pressure increments in common use. The amplifier 26 and A/D converter 24 could be made able to process oscillometric pulses after a 10 mm. change in cuff pressure if the gain of the differential amplifier 26 was reduced. However, reducing the gain of the differential amplifier would reduce the resolution with which the A/D converter 24 could process oscillometric pulses. The primary purpose of the invention is to be able to process oscillometric pulses following relatively large changes in cuff pressure without degrading the resolution with which the pulses are processed.

With continued reference to FIG. 1, the blood pressure monitor 10 also includes a software controlled voltage source 32 which supplies an offsetting voltage to the differential amplifier 26. As mentioned above, the output of the pressure transducer 20 is applied to the other input of the differential amplifier 26. The voltage output by the voltage source 32 offsets the voltage output by the pressure transducer 20 so that the voltage output by the differential amplifier 26 is preferably near the middle of its range (i.e., 2.5 volts, in the example given) but in any case is between the end points of its range (i.e., 0 volts and 5 volts, respectively, in the example given). The voltage that is output of the voltage source 32 is thus very close to the D.C. component of the pressure transducer 20.

A variety of conventional circuits may be used to implement the software controlled voltage source 32. In the presently preferred embodiment of the invention, the voltage source 32 is a digital-to-analog converter generating a voltage in the 0–5 volt range responsive to an 8 bit digital word. Thus, the voltage source 32 can generate 256 different analog voltages between 0 and 5 volts thereby providing a resolution of about 19.5 mv. (i.e., 5 v./256). The presently preferred embodiment of the invention would thus allow the cuff pressure to be changed in about 20 mm. increments and still allow the voltage source 32 to adjust the output of the amplifier 26 within the operating range of the A/D converter 24.

As also mentioned above, the microprocessor 22 is of conventional variety and, as is typical with such devices, is connected to a random access memory 34 which is used for the storage of data, and to either random access memory or read-only memory 36 which contains the software for operating the microprocessor 22. Operator controls 38, such as a keyboard or buttons, are also connected to the microprocessor 22.

Figure 2:
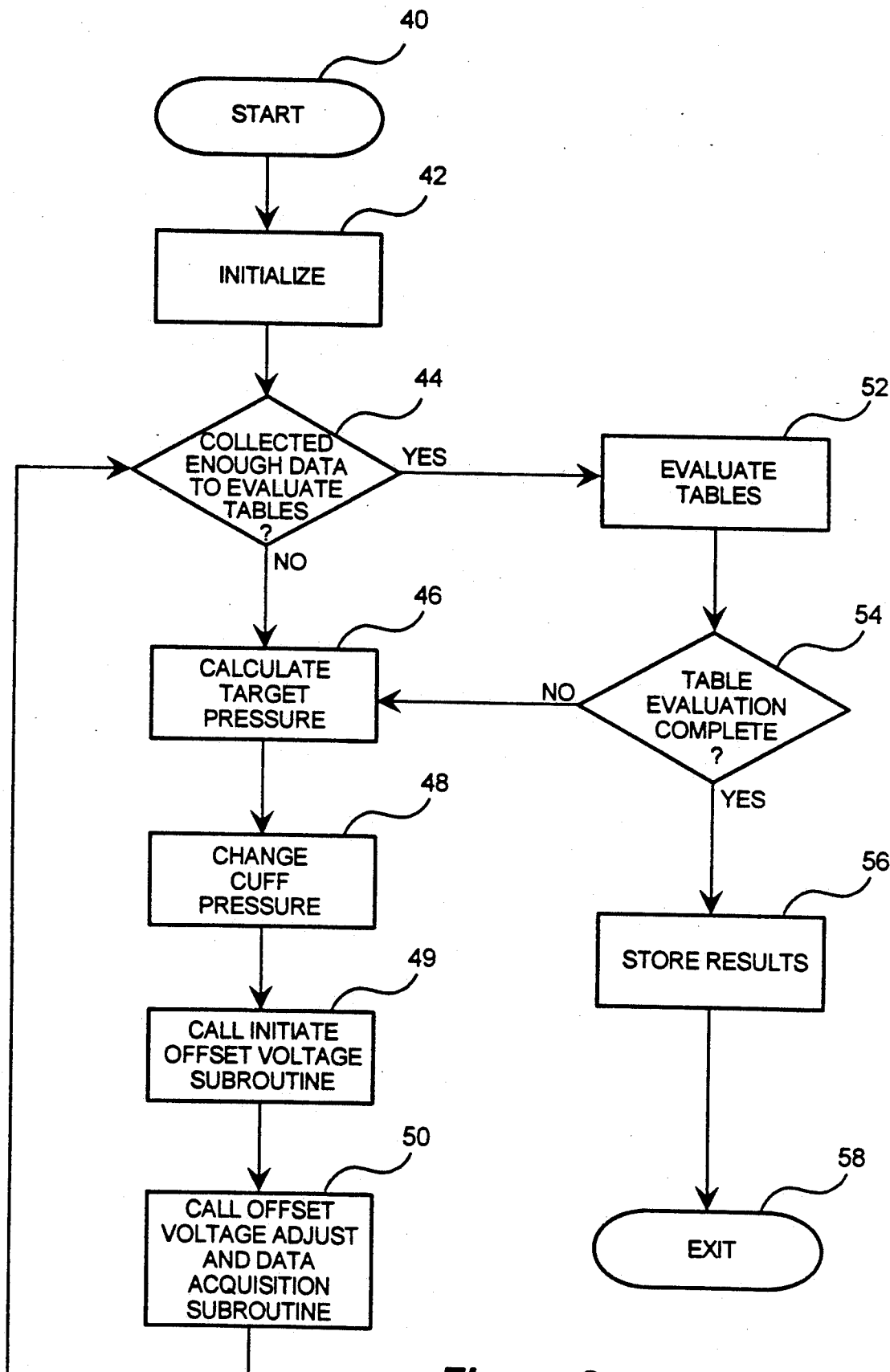
FIG. 2 is a flow chart of a main computer program used to program a microprocessor used in the automatic blood pressure monitor of FIG. 1.
Figure 3:
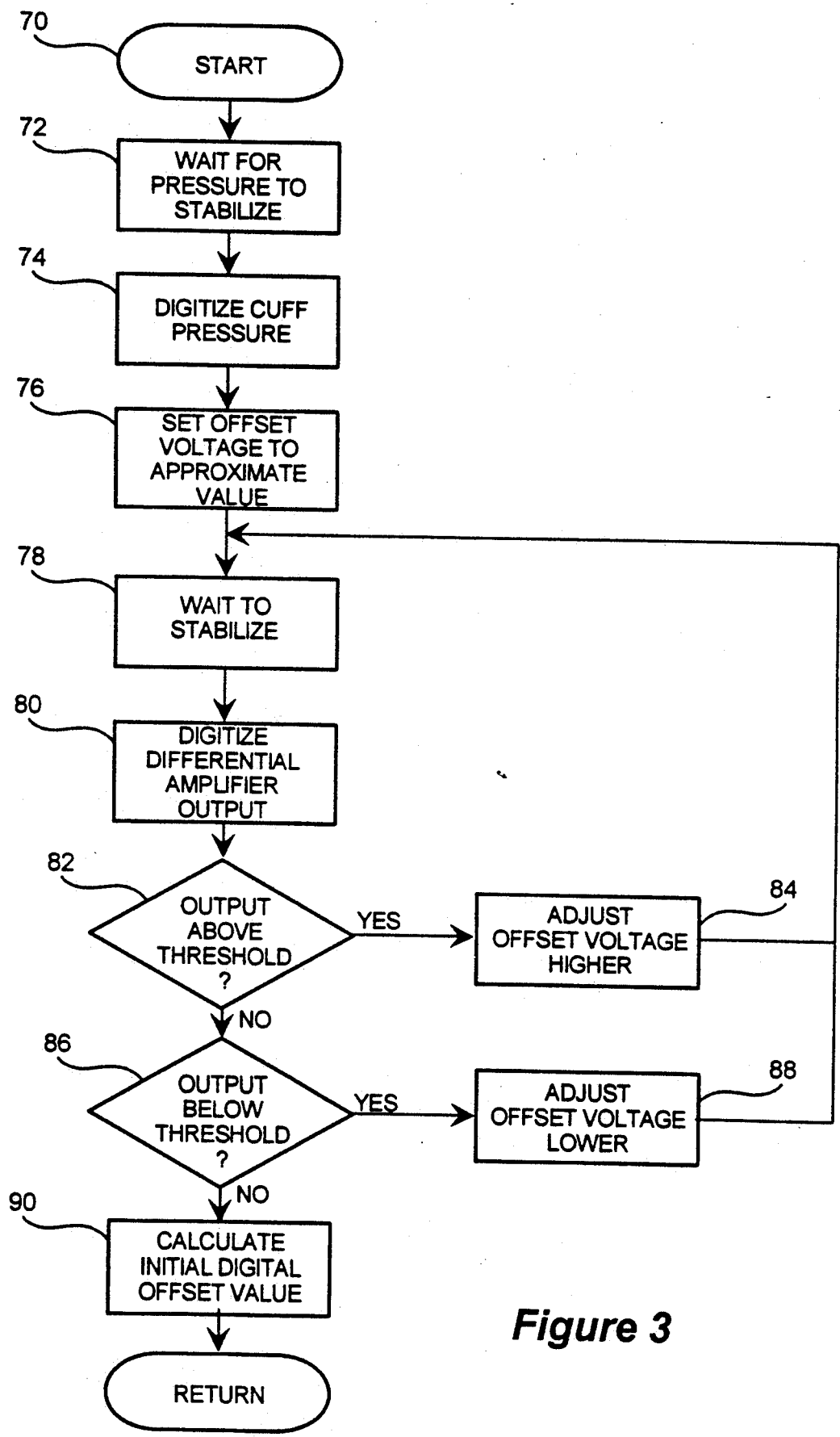
FIG. 3 is a flow chart of one embodiment of an initial offset subroutine called by the main computer program shown in FIG. 2.

The microprocessor 22 is controlled by software that is stored as a series of program instructions in the memory 36. A flow chart from which object code can be easily and quickly written by one skilled in the art is illustrated in FIGS. 2-4. With reference to FIG. 2, a main program starts at 40 either through an operator command, automatically at power-up, or when called by another program stored in the memory 36. As is conventional with microprocessor-based systems, the microprocessor 22 (FIG. 1) is initialized at 42 to set up the software for subsequent processing, such as, for example, by establishing tables that subsequently will contain data, by setting flags, and by setting variables to known values. The program then checks at 44 to determine if enough oscillometric pulse amplitude data have been collected in oscillometric data tables for evaluation.

The decision block 44 is first encountered prior to obtaining any oscillometric pulse amplitude data. Thus, when the program initially encounters decision block 44, the tables will not contain enough data to be evaluated. As a result, the program will branch to 46 to calculate a target value for the pressure in the blood pressure cuff 12 (FIG. 1). The target pressure for the cuff 12 will, of course, be in excess of the cuff pressure before the measurement is started. The microprocessor 22 then energizes the pump 16 (FIG. 1) at 48 while the output of the pressure transducer 20 is digitized by the A/D converter 24. The frequency of the digitization is controlled in a conventional manner by a conventional clock driven interrupt routine (not shown). A conventional filtering algorithm may be applied to the digitized signal in order to eliminate random noise from the resulting cuff pressure. The microprocessor 22 continues to energize the pump 16 at 48 until the cuff pressure is equal to the target pressure. On subsequent passes through steps 46 and 48, the target pressure calculated at 46 will be lower than the pressure in the cuff 12, so that the microprocessor 22 will energize the solenoid valve 18 at 48 to reduce the pressure in the cuff 12 to the target pressure.

Upon reaching the desired pressure, the main program calls an initial offset voltage subroutine at step 49. The initial offset voltage subroutine software determines the initial offset voltage, i.e., the initial output from the software controlled voltage source 32. The initial offset voltage subroutine is more fully described below with reference to FIG. 3.

After return from the initial offset voltage subroutine at step 49, the main program calls an offset voltage adjust and data acquisition subroutine at step 50 which is fully explained with reference to FIG. 5. Briefly, the offset voltage adjust and data acquisition subroutine provides further adjustments of the offset voltage applied to the differential amplifier 26, and it determines the oscillometic signal at the output of the A/D converter 24. The offset voltage is adjusted from the initial offset voltage by sampling the oscillometric signal at the output of the differential amplifier 26. If the oscillometric signal is near one of the boundaries of the input range of the A/D converter 24 as discussed above, an adjustment is made to the offset voltage generated by the software controlled voltage source 32. The offset voltage adjust and data acquisition subroutine also determines the oscillometic signal at the output of the A/D converter 24 by periodically sampling the output of the A/D converter 24 and compensating for the effect of the offset voltage on the output of the A/D converter 24 so that the calculated value of the oscillometric signal will be independent of the value of the offset voltage. As mentioned above, these functions of the offset voltage adjust and data acquisition subroutine are fully explained below with reference to FIG. 5.

When sufficient data are collected and averaged at a given cuff pressure, control returns from the offset voltage adjust and data acquisition subroutine at 50, and the main program then returns to 44 where a decision is once again made as to whether or not enough data have been collected to evaluate the tables and determine a blood pressure. The answer once again will be negative on the second pass though step 44. Therefore, the program will loop through 44, 46, 48, and 50 until sufficient data are collected. Each time the program proceeds through 46 and 48, the pressure in the cuff is decreased, usually in fixed steps, and the new offset voltage is acquired.

The program continues to loop through 44, 46, 48, and 50 (FIG. 2) until at a determination is made at step 44 that there are sufficient data in the oscillometric tables to permit evaluation of the table so that a blood pressure value can be determined. The program then branches to 52 where the tables are evaluated. At step 54, the table evaluation is judged to be either complete or incomplete. If incomplete, the program branches from step 54 to step 46 in order to collect more data.

If the table evaluation at is judged to be complete at step 54, then the program branches to step 56 where the results of the evaluation are stored. The table evaluation results in either (a) a blood pressure, or (b) an indication that there were too many artifacts to obtain a blood pressure. Upon completion of a measurement attempt, the program can also adjust parameters, such as screening and trigger levels, which may aid in collection of the next blood pressure. In any event, after the program displays and stores the results at step 56, it exits to the calling procedure at 58.

FIG. 3 is a flow chart of a subroutine for the initial offset voltage acquisition subroutine. At the end of every pump or bleed at step 48, the main program calls the initial offset acquisition subroutine which it entered at step 70. The subroutine then waits at step 72 for a short time to allow pneumatic settling, i.e. to allow pressure transients resulting from the relatively large change in cuff pressure to decay. After the delay, the subroutine enters step 74 in which the microprocessor 22 (FIG. 1) causes the A/D converter 24 to digitize the cuff pressure signal at the output of the pressure transducer 20, thereby determining the D.C. level of the output of the pressure transducer 20 after being boosted by the amplifier 23.

As mentioned above, in order to offset the oscillometric signal at the output of the differential amplifier 26 to near the mid-range of the A/D converter 24, the D.C. value of the pressure transducer output must, in effect, be subtracted from the be pressure transducer output. The digitized output of the differential amplifier 26 obtained at step 74 is thus used in step 76 to set an approximate initial value of the offset voltage to be generated by the software controlled voltage source 32. Accordingly, at step 76 the microprocessor 22 (FIG. 1) outputs a digital word to the voltage source 32 to cause the voltage source 32 to generate a voltage having a magnitude approximately equal to the D.C. value of the cuff pressure signal at the output of the pressure transducer 20, which was sampled at step 74. Since the differential amplifier 26 offsets the output of the pressure transducer 20 by the output of the voltage source 32, the resulting output of the differential amplifier 26 should be within the operating range of the A/D converter 24. After the initial offset voltage has been determined and the software controlled voltage source adjusted accordingly, the subroutine loops at 78 to allow the software controlled voltage source 32 to stabilize.

The subroutine then digitizes the output of the differential amplifier at 80, i.e. after the amplified output of the pressure transducer 20 has been offset by the initial offset voltage from the voltage source 32. The digitized value is then compared to a threshold at step 82. The threshold used at step 82 is preferably near the upper limit of the operating range of the A/D converter 24. In the presently preferred embodiment of the invention, this upper threshold is set at ¾ of full scale value, i.e., a digital output value of 768 which is three quarters of 1024 ($1024 = 2^{10}$) corresponding to an input of 3.75 volts. If the output of the differential amplifier 26 is above this threshold, the subroutine branches to 84. The subroutine then causes the microprocessor 22 to adjust the initial offset voltage generated by the software controlled voltage source 32 so that the output of the voltage source 32 is closer to the amplified output of the pressure transducer 20. The offset voltage generated by the voltage source 32 will therefore bring the output of the differential amplifier 26 closer toward the center of the operating range of the A/D converter 24. The subroutine then loops back to step 78.

If the output of the differential amplifier 26 was found to be below the upper threshold at step 82, the subroutine proceeds to 86 where the digitized output of the differential amplifier 26 is compared to a threshold that is near the lower limit of the operating range of the A/D converter 24. In the presently preferred embodiment of the invention, this lower threshold is set at ¼ of full scale value, i.e., a digital output value of 256 which is one quarter of 1026 corresponding to an input of 1.25 volts. If the output of the differential amplifier 26 is below this lower threshold, the subroutine branches to 88. The subroutine then causes the microprocessor 22 to adjust the offset voltage generated by the software controlled voltage source 32 so that the output of the voltage source 32 is closer to the amplified output of the pressure transducer 20. The adjusted offset voltage from the voltage source 32 will therefore bring the output of the differential amplifier 26 closer toward the center of the operating range of the A/D converter 24. The subroutine then loops back to step 78.

Either initially or after the output of the voltage source 32 has been adjusted as described above, the program will determine at steps 82 and 86 that the output of the differential amplifier 26 is below the upper threshold and above the lower threshold, respectively. The subroutine will then proceed to step 90 to calculate a digital offset value that compensates for the offset voltage so that the value of the oscillometric signal used to determine blood pressure will be insensitive to the value of the offset voltage. The rational for the digital offset value is best understood with references to FIGS. 4A and 4B.

Figure 4A:
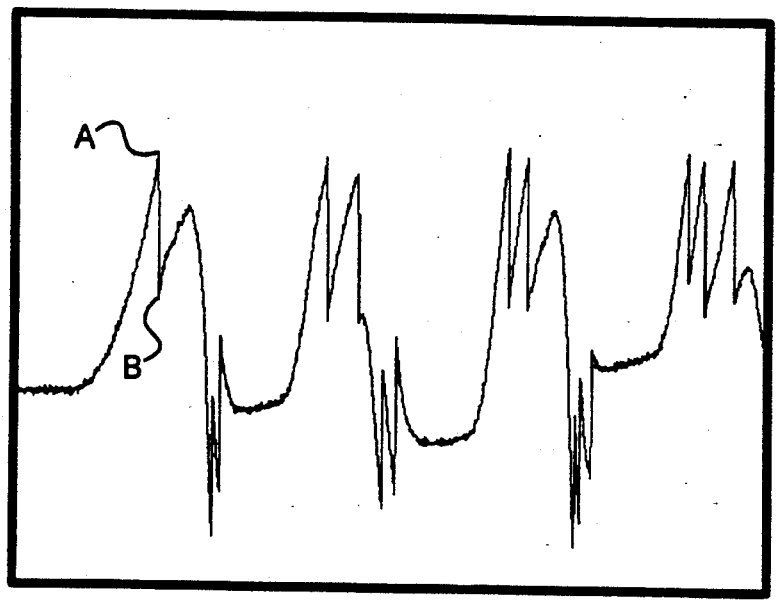
FIGS. 4A and 4B are diagrams showing waveforms obtained in the presently preferred embodiment of an automatic blood pressure monitor of FIG. 1.
Figure 4B:
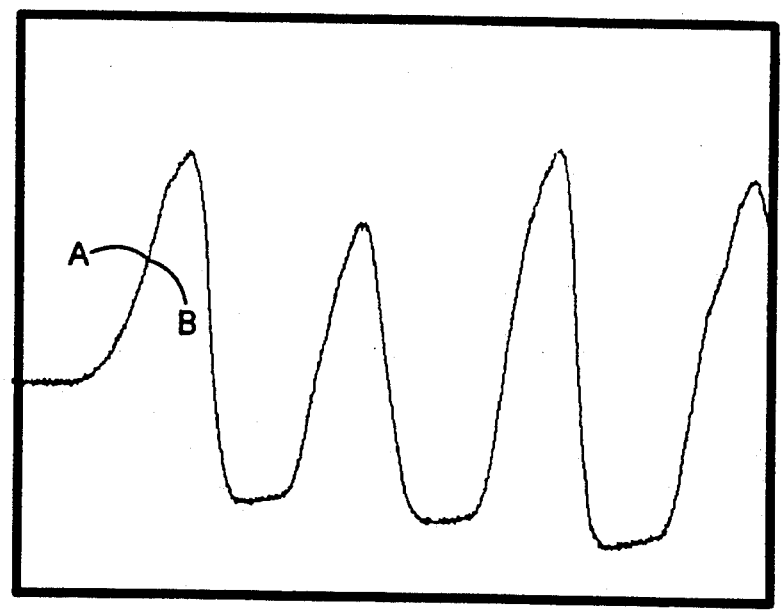

FIG. 4A shows the output of the differential amplifier 26 as a function of time. At point A, an adjustment is made to the offset voltage, thereby causing a step change in the output of the differential amplifier 26 that is applied to the A/D converter 24 from point A to point B. If the microprocessor 22 read the output of the A/D converter 24 as being truly indicative of the oscillometric signal, then the microprocessor 22 would erroneously determine that the oscillometric signal changed suddenly at point A. Thus, the microprocessor 22 must be able to compensate for or cancel out the changes in the output of the A/D converter 24 that are due to changes in the offset voltage in order to determine the true oscillometric signal. As a result, the oscillometric signal reconstructed by the microprocessor, which is shown in FIG. 4B, has the same value at A (before the offset voltage adjustment) as it has at point B (after the offset voltage adjustment).

The above-described compensation is accomplished by the microprocessor 22 initially setting a digital offset value to an arbitrary value, such as 4000 hex which corresponds to 16,384 decimal. If, for example, the output of the A/D converter 24 is 810 at point A, an oscillometric value calculated by adding 810 to the initial digital offset of 16,384 is 17,194. However, the 810 output of the A/D converter 24 is above the 768 upper threshold used in the above example. As a result, the offset voltage output by the software controlled voltage source 32 would be increased to reduce the input to the A/D converter 24. If the offset voltage is adjusted down to point B, the output of the A/D converter 24 might now be, for example, 600. The difference between the outputs of the A/D converter at points A and B would thus be 168 (i.e., 768 less 600). The microprocessor 22 then adjusts the digital offset by this amount so that the new digital offset is now 16,594 decimal (i.e., 16,384+810−600). However, the new value of the A/D converter output at point B is, as mentioned above, 600 which, when added to the new digital offset of 16,594, is 17,194. This new oscillometric value of 17,194 at point B is the same as the old oscillometric value of 17,194 obtained by summing the initial digital offset of 16,384 with the 810 output of the A/D converter 24 at point A. Thus, the microprocessor 22 is able to calculate the same oscillometric value at points A and B despite the abrupt change in the signal applied to the A/D converter 24.

Figure 5:
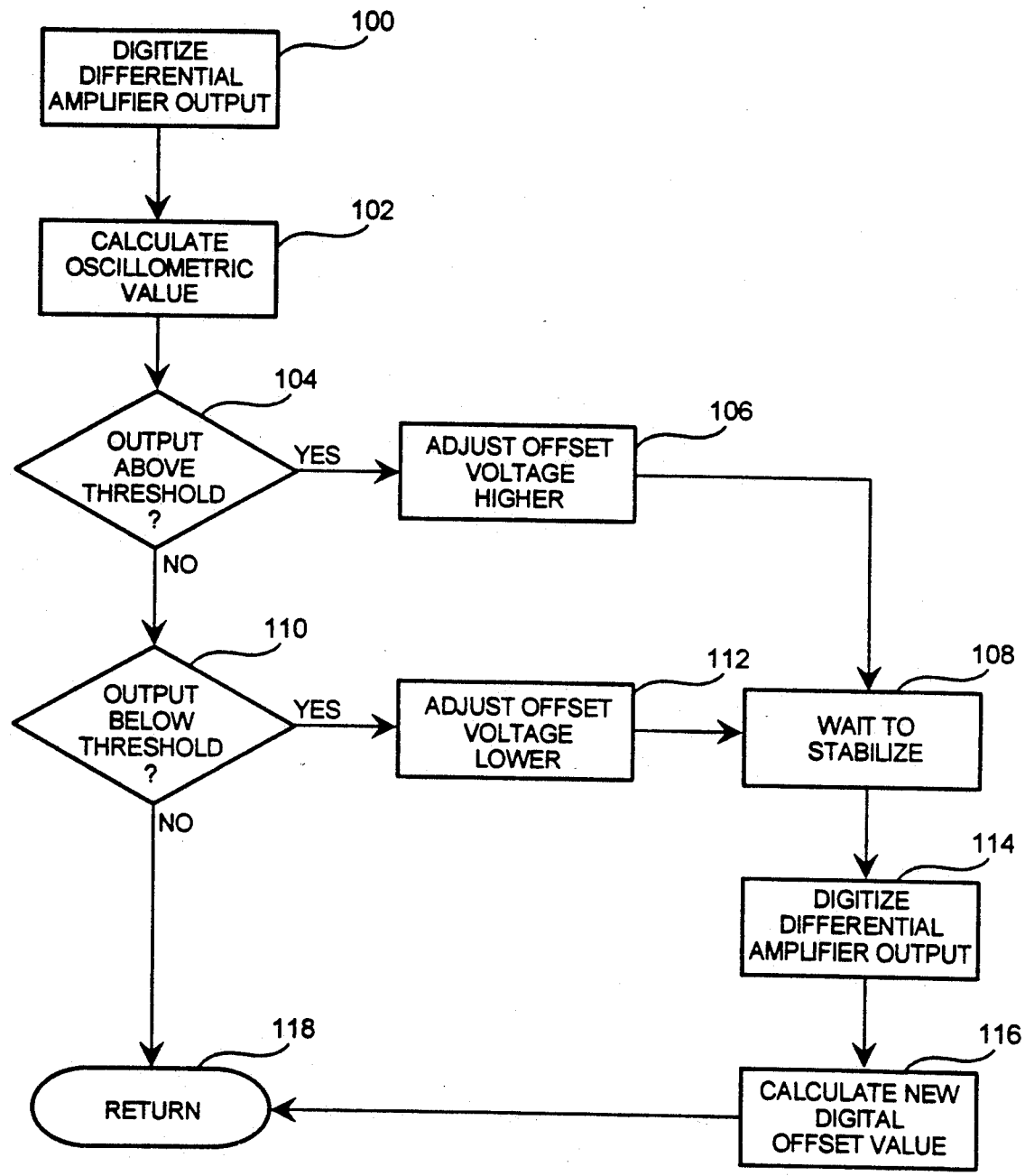
FIG. 5 is a flow chart of one embodiment of a subroutine called by the main computer program shown in FIG. 2 for adjusting the initial offset set by the subroutine of FIG. 3 and for collecting data samples.

FIG. 5 is a flow chart of a subroutine called by the main program at step 50 (FIG. 2) to adjust the offset voltage from the initial value, to collect data samples of the oscillometric signal at the output of differential amplifier 26, and to calculate oscillometric values in order to reconstruct the true oscillometric signal. At step 100, the microprocessor 22 causes the digital-to-analog converter 24 to generate a digitized sample of the output of the differential amplifier 26. An oscillometric value corresponding to the true oscillometric signal when the sample is taken is then calculated at 102 by adding the digital word at the output of the A/D converter 24 to the initial digital offset value calculated by the subroutine explained above with reference to FIG. 3. The result of this addition is stored in the random access memory 34 for use by the analysis portion of the program in step 50.

The subroutine then proceeds to step 104 where the output of the A/D converter 24 obtained at 100 is compared to an upper threshold that is near the upper limit of the operating range of the A/D converter 24. If the output of the analog-to-digital converter 24 is above this threshold, the subroutine branches to 106 where an adjustment is made to the software controlled voltage source 32 so that the output of the voltage source 32 is closer to the output of the pressure transducer 20. The adjusted output from the voltage source 32 will therefore bring the output of the differential amplifier 26 beneath the upper threshold and closer toward the center of the operating range of the analog to digital converter 24. The subroutine then proceeds to step 108 which is discussed below.

If the output of the differential amplifier 26 was found to be below the upper threshold at step 102, the subroutine proceeds to 110 where the digitized output of the differential amplifier 26 is compared to a lower threshold that is near the lower limit (i.e. negative voltage limit) of the operating range of the A/D converter 24. If the output of the differential amplifier 26 is below the lower threshold, the subroutine branches to 112. The subroutine then causes the microprocessor 22 to adjust the output of the software controlled voltage source 32 so that the output of the voltage source 32 is above the lower threshold and closer to the output of the pressure transducer 20. The adjusted output from the voltage source 32 will therefore bring the output of the differential amplifier 26 closer toward the center of the operating range of the analog to digital converter 24. The subroutine then proceeds to step 108 which is discussed below. If the subroutine determined at step 110 that no adjustment of the software controlled voltage source 32 was required, the subroutine returns to the main program of FIG. 2 via step 118.

If the subroutine determined at either step 104 or step 110 that adjustment of the software controlled voltage source 32 was required, then the subroutine waits at 108 to allow the software controlled voltage source 32 to stabilize. After the delay, the subroutine proceeds to 114 where the microprocessor 22 causes the A/D convertor 24 to generate a digitized sample of the output of the differential amplifier 26.

It will be recalled that the subroutine had previously generated a digitized sample of the output of the differential amplifier 26 at step 100. Thus, the subroutine obtains two digitized samples each time the offset voltage applied to the differential amplifier is to be adjusted. However, the time between obtaining the digitized sample at 100 and obtaining the digitized sample at 114 is sufficiently short in relation to the frequency spectrum of the output of the pressure transducer 20 so that the two digitized samples should be substantially the same. Therefore, any significant difference between the digitized sample obtained at 100 and the digitized sample obtained at 114 must be due to the change in the value of the offset voltage. Using the example explained above with reference to FIGS. 4A and 4B, the sample obtained at step 100 would be 810, and the sample obtained at 114 would be 600. The subroutine of FIG. 5 calculates a new digital offset value as explained above by summing the 210 difference with the current digital offset value (e.g., 16,384) to obtain the new offset value (e.g., 16,594). The subroutine then returns to the main program through 118.

The offset voltage generated by the voltage controlled voltage source 32 is thus set by the subroutine of FIG. 3 to an initial offset value each time the pressure in the cuff 12 changes, and it is then adjusted as needed by the subroutine of FIG. 5 each time an oscillometric sample is taken at that cuff pressure. Each time that the subroutine of FIG. 5 is executed, the digital offset value calculated during the previous pass through the subroutine of FIG. 5 will be used at step 102 to calculate a new oscillometric value, and, if the offset voltage was adjusted, a new digital offset value is calculated at step 116.

It is thus seen that the inventive blood pressure monitor is capable of accurately measuring oscillometric pulses despite relatively large changes in sampled cuff pressure caused by cuff pressure changes, motion artifact, and pneumatic leaks. Furthermore, the inventive monitor is able to do so without requiring the use of an A/D converter having an extraordinary large dynamic range.

I claim:

1. An improved method for use in a blood pressure monitor of the type having a blood pressure cuff, an air pump in fluid communication with said cuff to direct pressurized air into said cuff, an air valve in fluid communication with said cuff to selectively vent said cuff to atmosphere, a pressure transducer in fluid communication with said cuff generating a pressure signal indicative of the steady state fluid pressure in said cuff corresponding to an occlusive pressure exerted by said cuff on an artery and a transient fluid pressure in said cuff indicative of the amplitude of an oscillometric waveform, a processor in electrical communication with said air pump and said air valve for selectively energizing said air pump or valve to pressurize or depressurize said cuff, respectively, said method allowing said oscillometric waveform to be sampled despite relatively large changes in the steady state fluid pressure in said cuff, said method comprising:

setting the steady state fluid pressure in said cuff to a predetermined value;

sampling the pressure signal output by said pressure transducer resulting from the steady state fluid pressure in said cuff, and generating an offset signal corresponding thereto;

subtracting said offset signal from the pressure signal output by said pressure transducer, thereby generating an offset pressure signal;

sampling said offset pressure signal;

generating a plurality of digital numbers corresponding to a respective plurality of samples of said offset pressure signal; and analyzing said digital numbers to determine blood pressure.

2. The method of claim 1 further including the step of adjusting magnitude of said offset signal by the steps of:

comparing each digital number to a predetermined range of said digital numbers; and adjusting said offset signal in the event that said digital number is outside a predetermined range of said digital numbers so that said offset pressure signal corresponds to a value that is closer to the center of said predetermined range of said digital numbers.

3. An improved method for use in a blood pressure monitor of the type having a blood pressure cuff, an air pump in fluid communication with said cuff to direct pressurized air into said cuff, an air valve in fluid communication with said cuff to selectively vent said cuff to atmosphere, a pressure transducer in fluid communication with said cuff generating a pressure signal indicative of the steady state fluid pressure in said cuff corresponding to an occlusive pressure exerted by said cuff on an artery and a transient fluid pressure in said cuff indicative of the amplitude of an oscillometric waveform, a processor in electrical communication with said air pump and said air valve for selectively energizing said air pump or valve to pressurize or depressurize said cuff, respectively, said method allowing said oscillometric waveform to be sampled despite relatively large changes in the steady state fluid pressure in said cuff, said method comprising:

setting the steady state fluid pressure in said cuff to a predetermined value;

sampling the pressure signal output by said pressure transducer resulting from the steady state fluid pressure in said cuff, and generating an initial offset signal corresponding thereto;

subtracting said initial offset signal from the pressure signal output by said pressure transducer, thereby generating an initial offset pressure signal;

sampling said initial offset pressure signal, and generating an initial digital number corresponding thereto;

determining an initial digital offset value;

adding said initial digital offset value to said initial digital number, thereby generating an initial oscillometric value;

continuing to subtract said initial offset signal from the pressure signal output by said pressure transducer, thereby generating a continuous offset pressure signal;

periodically sampling said continuous offset pressure signal, and generating a respective digital numbers corresponding thereto;

adjusting the value of said initial offset signal if said offset signal falls outside a predetermined range;

after each adjustment of said initial offset signal, calculating a new digital offset value by summing the prior digital offset value to the difference between two of said digital numbers taken at successive times;

adding said new digital offset value to each of said digital numbers, thereby generating a plurality of oscillometric values;

analyzing said oscillometric values to determine blood pressure.

4. An improved method for use in a blood pressure monitor of the type having a blood pressure cuff, an air pump in fluid communication with said cuff to direct pressurized air into said cuff, an air valve in fluid communication with said cuff to selectively vent said cuff to atmosphere, a pressure transducer in fluid communication with said cuff generating a pressure signal indicative of the steady state fluid pressure in said cuff corresponding to an occlusive pressure exerted by said cuff on an artery and a transient fluid pressure in said cuff indicative of the amplitude of an oscillometric waveform, a processor in electrical communication with said air pump and said air valve for selectively energizing said air pump or valve to pressurize or depressurize said cuff, respectively, said method allowing said oscillometric waveform to be sampled despite relatively large changes in the steady state fluid pressure in said cuff, said method comprising:

setting the steady state fluid pressure in said cuff to a predetermined value;

sampling the pressure signal output by said pressure transducer resulting from variations in the fluid pressure in said cuff caused by oscillometric pressure pulses, and generating a pressure signal corresponding thereto;

offsetting said pressure signal by an offset value, thereby generating an offset pressure signal;

periodically sampling said offset pressure signal and generating respective digital numbers corresponding thereto;

summing each of said digital numbers with an offset value, thereby generating respective oscillometric values;

adjusting the magnitude of said offset pressure signal if said offset value falls outside a predetermined range;

after each adjustment of said offset value, calculating a new offset value by summing the prior offset value with the difference between two of said digital numbers taken at successive times;

analyzing said oscillometric values to determine blood pressure.

5. A blood pressure monitor, comprising:

a blood pressure cuff;

a pneumatic controller in fluid communication with said cuff to selectively vary a fluid pressure in said cuff responsive to a pneumatic control signal;

a pressure transducer in fluid communication with said cuff, said pressure transducer generating a pressure signal indicative of the fluid pressure in said cuff corresponding to an occlusive pressure exerted by said cuff on an artery and a transient fluid pressure in said cuff indicative of the amplitude of an oscillometric waveform;

voltage generating means for generating an offset voltage corresponding to a steady state pressure in said cuff;

offset means coupled to said voltage generating means and to said pressure transducer for generating an offset pressure signal corresponding to the difference between the pressure signal output by said pressure transducer and said offset voltage;

analog-to-digital converter means having a predetermined operating range coupled to said offset means, said analog-to-digital converter means sampling said offset pressure signal, thereby generating a plurality of digital numbers corresponding to a respective plurality of samples of said offset pressure signal; and processing means in electrical communication with said pneumatic controller for generating said pneumatic control signal to cause said pneumatic controller to vary the fluid pressure in said cuff, said processing means being connected to an output of said analog-to-digital converter means to receive said digital numbers and analyze said samples to determine the blood pressure in an artery beneath said cuff whereby oscillometric pressure pulses imparted to said cuff can be sampled despite relatively large changes in the steady state fluid pressure in said cuff.

6. The blood pressure monitor of claim 5 wherein said offset means amplifies changes in the magnitude of said pressure signal, and wherein said analog-to-digital converter means receives said pressure signal as well as said offset pressure signal, said processing means causing said voltage generating means to initially generate said offset voltage from said pressure signal.

7. The blood pressure monitor of claim 5 wherein said processing means further includes means for adjusting the magnitude of said pressure offset signal by comparing each sample of said offset pressure signal to the operating range of said analog-to-digital converter means, and then adjusting said pressure offset signal in the event that a sample of said offset pressure signal is outside a predetermined portion of the operating range of said analog-to-digital converter means so that said offset pressure signal is closer to the center of the operating range of said analog-to-digital converter means.

8. The blood pressure monitor of claim 5 wherein said processing means includes means for adjusting the magnitude of said offset voltage generated by said voltage generating means if said offset voltage falls outside a predetermined portion of the operating range of said analog-to-digital converter means.

9. The blood pressure monitor of claim 8 wherein said processing means includes means for calculating oscillometric signal samples from said digital numbers, comprising:

means for summing each of said digital numbers with an offset value, thereby generating respective oscillometric signal samples; and after each adjustment of said offset value, calculating a new offset value by summing the prior offset value with the difference between two of said digital numbers taken at successive times.

* * * * *

UNITED STATES PATENT AND TRADEMARK OFFICE
CERTIFICATE OF CORRECTION

PATENT NO. : 5,280,790
DATED : January 25, 1994
INVENTOR(S) : James R. Brooks

It is certified that error appears in the above-indentified patent and that said Letters Patent is hereby corrected as shown below:

In column 11, claim 3, line 65, please delete "numbers" and substitute therefor --number--.

In column 14, claim 9, line 29, after "between" and before "two of", please insert --the preceding--.

Signed and Sealed this

Twenty-third Day of August, 1994

Attest:

BRUCE LEHMAN

Attesting Officer    Commissioner of Patents and Trademarks